United States Patent
Mass et al.

[19]

[11] Patent Number: 6,054,097
[45] Date of Patent: Apr. 25, 2000

[54] EXPANDING PLASMA EMISSION SOURCE MICROORGANISM INACTIVATION SYSTEM

[75] Inventors: Barton Mass, San Jose; Robert LaFrenz, El Cajon; David LaFrenz, La Mesa, all of Calif.

[73] Assignee: Innovatech, El Cajon, Calif.

[21] Appl. No.: 09/128,262

[22] Filed: Aug. 3, 1998

[51] Int. Cl.[7] .............................. A61L 2/08; A61L 2/10
[52] U.S. Cl. ...................... 422/24; 422/22; 422/186.3; 422/305; 422/900; 422/905; 422/906; 210/748; 250/493.1; 250/504 R
[58] Field of Search .............................. 422/22, 24, 186, 422/186.3, 305, 900, 905, 906; 210/748; 250/493.1, 496.1, 503.1, 504 R

[56] References Cited

U.S. PATENT DOCUMENTS

| | | | |
|---|---|---|---|
| 4,304,996 | 12/1981 | Blades | 250/373 |
| 4,464,336 | 8/1984 | Hiramoto | 422/24 |
| 4,467,206 | 8/1984 | Taylor et al. | 422/24 |
| 4,728,368 | 3/1988 | Pedziwiatr | 422/24 |
| 4,871,559 | 10/1989 | Dunn et al. | 422/24 |
| 5,213,759 | 5/1993 | Castberg et al. | 422/24 |
| 5,635,059 | 6/1997 | Johnson | 422/186.3 |
| 5,685,994 | 11/1997 | Johnson | 210/748 |

*Primary Examiner*—Robert J. Warden, Sr.
*Assistant Examiner*—Fariborz Moazzam
*Attorney, Agent, or Firm*—Frank D. Gilliam

[57] ABSTRACT

A method and apparatus for disinfecting material such as a fluid stream, (e.g., water) or various objects (e.g., packaging, fruits, vegetables) using a high temperature expanding plasma emission source (EPES lamp) to generate intense pulses of ultraviolet light primarily in the 200–400 nm range. The EPES lamp is preferably mounted axially in a pipe through which the fluid to be disinfected is flowed or perpendicular to the direction of a fluid flow or an object conveyor. Each pulse is terminated before the resulting plasma within the EPES lamp reaches the inside surface of the EPES lamp wall so that the EPES lamp operates in an expanding plasma emission source mode rather than in a wall stabilized mode. The EPES lamp is operated at a plasma temperature of at least about 15,000° K. and an energy density (Q) of at least about 300.

14 Claims, 4 Drawing Sheets

EXPANDING PLASMA EMISSION SOURCE MICROORGANISM INACTIVATION SYSTEM

FIELD OF THE INVENTION

This invention relates to the photochemical inactivation of microorganisms on surfaces or in fluids and more particularly to treating a surface or fluid with pulsed ultraviolet light to inactivate microorganisms.

BACKGROUND OF THE INVENTION

A wide variety of methods have been used over the years to purify water to produce potable water from a contaminated water source or to disinfect the outer surfaces of foods such as fruit and food packaging. Purification of water is becoming an increasing problem because of the increasing levels of contamination in many water sources. Similarly, disinfecting products such as fruit, vegetables and the like to eliminate microorganisms that can contaminate the products during growing handling and shipping, particularly with long distance shipping of such products.

Municipal water supplies have generally been purified by a combination of methods, including filtering the water and treating the water with chlorine. Other agents are being used to varying degrees, such as treatment with ozone gas, administration of various types of radiation, including ionizing radiation, thermal methods and the like.

Ultraviolet light (UV) is an effective disinfecting or sterilizing agent with few, if any, side effects. A UV radiating plasma is highly effective for treating surfaces, such as packaging and for fluids such as water. For example, Tensmeyer in U.S. Pat. No. 3,995,921 describes a process using a focused laser beam to generate UV with a pulsed plasma source to disinfect the interior of a container. However, the method disclosed is not useful for treating flowing fluids, such as water.

Copa, in U.S. Pat. No. 4,265,747, describes use of a laser beam to generate a UV radiating plasma for treatment of a fluid. However, its applicable to small volumes only. Hiramoto in U.S. Pat. No. 4,464,336 teaches the use of a wall stabilized flash lamp for sterilizing microorganisms. It is apparent from the Hiramoto disclosure that he uses a "wall stabilized" flash discharge lamp. In the wall stabilized mode of operation a plasma column expands and fills the entire quartz lamp during a capacitive discharge. The resulting operation of the system, and the pulsed light produced, is then dominated by the walls and the confined plasma. This prevents operating at higher temperatures, voltages and longer pulse widths as would be desirable to provide shorter, more effective UV wavelengths. A similar wall stabilized flashlamp plasma concept, having the same problems, is described by Dunn in U.S. Pat. No. 4,871,559 for treatment of food packaging.

Thus, there is a continuing need for improved systems for treating water and other fluids and various surfaces with UV that overcomes the limitations of wall stabilized flash discharge lamps, provides short pulse durations at shorter UV wavelengths and is highly effective in disinfecting a continuously flowing stream of water or other fluid.

SUMMARY OF THE INVENTION

The above-noted problems, and others, are overcome in accordance with this invention by a method and apparatus which utilizes a pulsed UV expanding plasma emission source (EPES lamp) of very high intensity and short duration to disinfect a material, such as a flowing fluid stream, surfaces of packaging, products such as fruits and vegetables and the like. A voltage typically of from about 3000 to 4000 volts is imposed on the EPES lamp electrodes to generate an expanding plasma pulse having a duration of from about 20 to 30 microseconds, the plasma temperature being from about 15,000 to 18,000° K., then repeating pulses at a frequency of up to about 30 Hz.

The pulse length is carefully chosen so that the plasma does not equilibrate with the EPES lamp interior wall surface and never becomes wall stabilized. The result of the elevated temperatures and voltages is to shift the black body emission spectrum of the plasma to shorter UV wavelengths. Optimally, the UV spectrum is tuned to peak in the 200 to 400 nanometer range. Thus, a large portion of the emission spectrum is in the range of photochemical interaction frequencies most effective in achieving maximum DNA absorption and organism inactivation. By providing a very high energy density, or "Q" as defined below, more efficient disinfection is obtained with the system of this invention.

The excitation circuit of this invention avoids use of inductors as used in wall stabilized flash discharge lamps, thus permitting the production of extremely short pulses, with durations of a few microseconds. This excitation arrangement provides for a nearly instantaneous application of a capacitor voltage to the EPES lamp electrodes. The resulting plasma excitation and photon emission process is essentially completed before the expanding plasma becomes limited by the quartz EPES lamp containment wall. At the higher temperatures provided in this EPES lamp, the plasma becomes a more efficient radiator and can dissipate energy which would lead to early failure of the EPES lamp if it were allowed to remain in contact and interact with the quartz walls. Here, the quartz EPES lamp is used only to contain the gas (e.g., xenon or krypton) and exclude other gases such as oxygen or water vapor. The walls do not define the plasma behavior.

For fluid treatment, the expanding plasma emission source flashlamp is coaxially with, or perpendicular to, the fluid flow, typically water flowing in a pipe. When treating surfaces of objects such as packaging or fruits and vegetables, the EPES lamp will preferably be oriented perpendicular to the direction of movement of a conveyor carrying the objects. The high intensity, short duration pulses of UV energy photochemically inactivate any microorganisms present in the fluid or on exposed surfaces of the objects. As used in this application, "material" means anything, fluid or solid, that will benefit from disinfection by the method and apparatus of this invention. Materials enjoying optimum benefits include flowing water, the surfaces of packaging materials, typically food packages, and foods that are not generally packaged, such as raw fruits, vegetables and the like.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
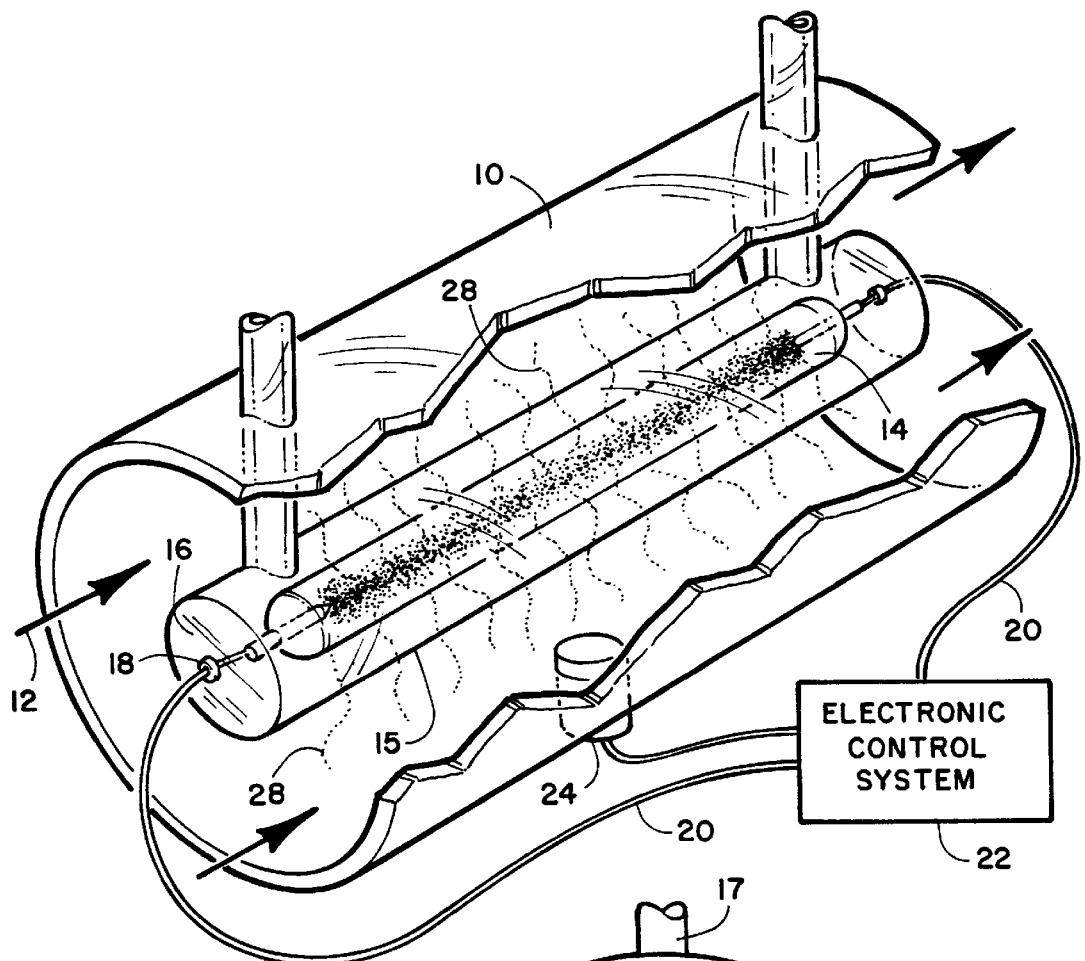
FIG. 1 is a schematic perspective view of a pulsed UV treatment chamber in accordance with this invention.
Figure 2:
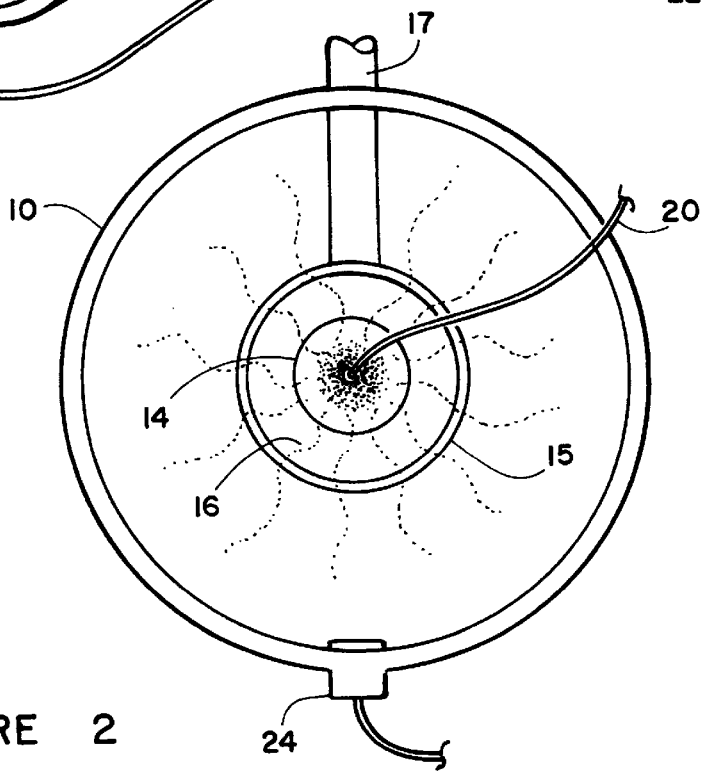
FIG. 2 is a schematic transverse end view of the chamber of FIG. 1.

Referring to FIGS. 1 and 2, there is seen a pipe 10, cut away to show inner components. Water (or other fluid to be disinfected) flows through pipe 10 in the direction of arrows 12. An EPES lamp 14 axially located within pipe 10 is held in place by conventional supports, not shown for clarity. A cooling jacket 16, formed from a larger quartz cylinder closed at the ends, encloses EPES lamp 14. Cooling water is passed through feed lines 17 into jacket 16 to cool EPES lamp 14 in use. EPES lamp ends 16 are closed, with an electrode 18 penetrating each end. Wires 20 extend from each electrode 18 to an electronic control system 22 (as detailed in FIG. 6) for operating EPES lamp 14. A sensor 24 may be provided through a side of pipe 10 to monitor UV within the pipe.

Figure 3A:
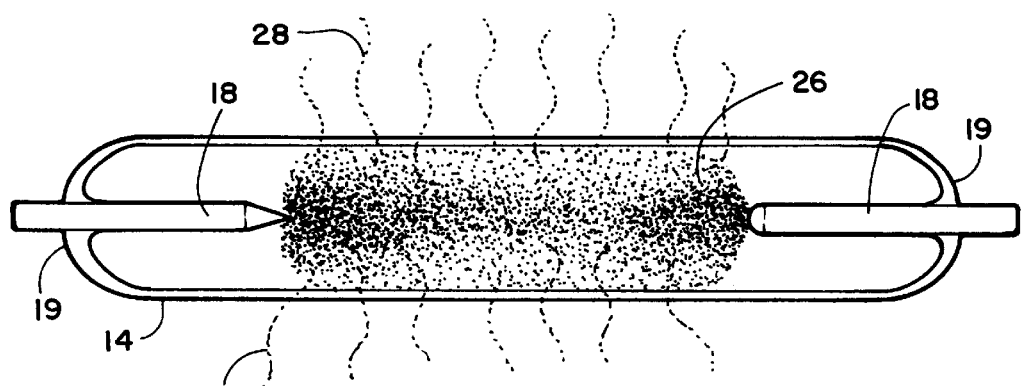
FIG. 3a schematically illustrates a flash lamp operating according to the prior art at low Q.

Any suitable expanding plasma emission source EPES lamp 14 may be used. EPES lamps are generally formed from quartz and must be highly transparent to UV. EPES lamp 14 contains an inert gas, preferably xenon or krypton. Ends 19 of EPES lamp 14 are hermetically sealed around metal electrodes 18 that extend through the sealed ends, as seen in FIGS. 3a and 3b.

Figure 3B:
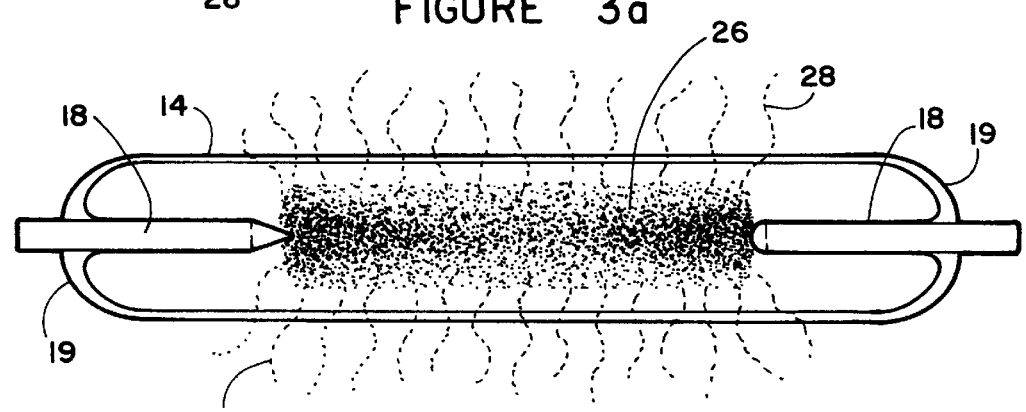
FIG. 3b schematically illustrates an EPES lamp operating according to the present invention at high Q.

FIGS. 1 and 3b show EPES lamp 14 just after initiation of plasma 26 within the EPES lamp between electrodes 18. The plasma is emitting of a very large number of schematically illustrated UV photons 28 into the water in pipe 10. As is discussed in detail below, plasma 26 will decay before growing large enough to equilibrate with the inner wall surface of EPES lamp 14. Subsequently, another flash will begin.

In a preferred embodiment for water treatment, EPES lamp 14 is mounted along the axis of a typically 6 to 12 inch diameter pipe 10. The pipe has a straight section at least 3 times the length of EPES lamp 14, centered on the EPES lamp. This permits maximum light pattern spread, to utilize the maximum proportion of the generated UV photons. A conventional manifold (not shown) is preferably used to force uniform flow across the cross section of the pipe. Additionally, the inlet assembly may impart a tangential component to the water so that flow through the chamber is high quality plug flow with a high degree of mixing from the center to the wall of pipe 10.

The EPES lamp is preferably housed within a quartz tube housing 15 with high UV transmission characteristics, such as the quartz tubes available from Heraeaus under the Suprasil® trademark. The EPES lamp 14 is preferably a quartz EPES lamp about 6 in. between the internal end electrodes 18. EPES lamp 14 is formed from a material such as Suprasil® 300 from Heraeaus, which has high UV transmission and is capable of withstanding the intense operating conditions for hundreds of millions of pulses.

Quartz housing tube 15 is spaced from EPES lamp 14 and the space therebetween is flooded with high quality low conductivity water (or other suitable cooling liquid) flowing typically at least about 1 gpm to keep the EPES lamp cooled.

EPES lamp 14 is filled with a rare gas, preferably xenon or krypton, typically at a pressure of about 700 Torr (with somewhat higher or lower pressures useful to vary performance). One electrode 18 is an anode and is preferably rounded and the other is a cathode, preferably pointed to provide long life.

EPES lamp 14 is ignited by a high voltage pulse applied to the exterior of the tube. A current of about 3 amps is maintained through EPES lamp 14 so as to maintain a well centered and well defined "simmer" arc. The EPES lamp is periodically pulsed, typically by applying approximately 3600 volts from a capacitor of about 20 microfarads. The capacitor discharges rapidly, over approximately 20 to 30 microseconds full width at half maximum causing the plasma to expand towards the walls of the EPES lamp and heating the plasma to a very high temperature. The expanding plasma emission source operates during the expanding phase of plasma and terminates before the plasma equilibrates with the wall of the EPES lamp.

Preferably very high energy loading is used during the pulse so as to drive the plasma to high temperature so that the black body radiation peaks at wavelengths in the UV range, typically between about 200 and 400 nm, with the ideal peak at about 260 nm. This pulsing is repeated at regular intervals up to approximately 30 Hz. Higher pulse rates may be used at the expense of shortened EPES lamp life.

FIG. 3a schematically illustrated the full development of a plasma 26 between electrodes in a prior art flash lamp 14 of the type generally identified as "wall stabilized flashlamps". As the name suggests, "wall stabilized" indicates that the plasma column 26 expands after electrodes 18 have been pulsed with energy from a capacitor and inductor system to fill the entire quartz flashlamp 14. The pulsed light spectrum is then dominated by the walls and the confined plasma. Operation in this mode precludes operating at temperatures higher than about 10,000° K. or achieving pulse lengths less than about 100 microseconds. This operational mode does not permit utilization of voltages greater than approximately 1500 v for a six inch lamp, so that the discharge has a relatively low "Q". These limitations occur because of material property limitations and basic plasma physics.

FIG. 3b schematically illustrates an EPES lamp 14 with electrodes 18 near the end of a pulse with plasma 26 at maximum diameter. This schematically illustrates the system being operated in the "expanding plasma emission source" manner of this invention. The EPES lamp electrodes 18 have been pulsed from a capacitor without discrete inductance. The total inductive impedance of the circuit is small compared to the lamp resistive impedance. By using a very short pulse, on the order of a few tens of microseconds, the entire plasma excitation and photon emission process peaks and decays before the expanding plasma becomes limited by the containment wall. Since the plasma does not encounter and erode the EPES lamp walls, very high voltages in a range of about 3000 to 5000 v for a six inch EPES lamp and temperatures in the range of about 15,000 to 18,000° K. may be used. A much greater number of photons 28 result and are further into the photochemical microorganism disinfection region of the UV spectrum.

Figure 4:
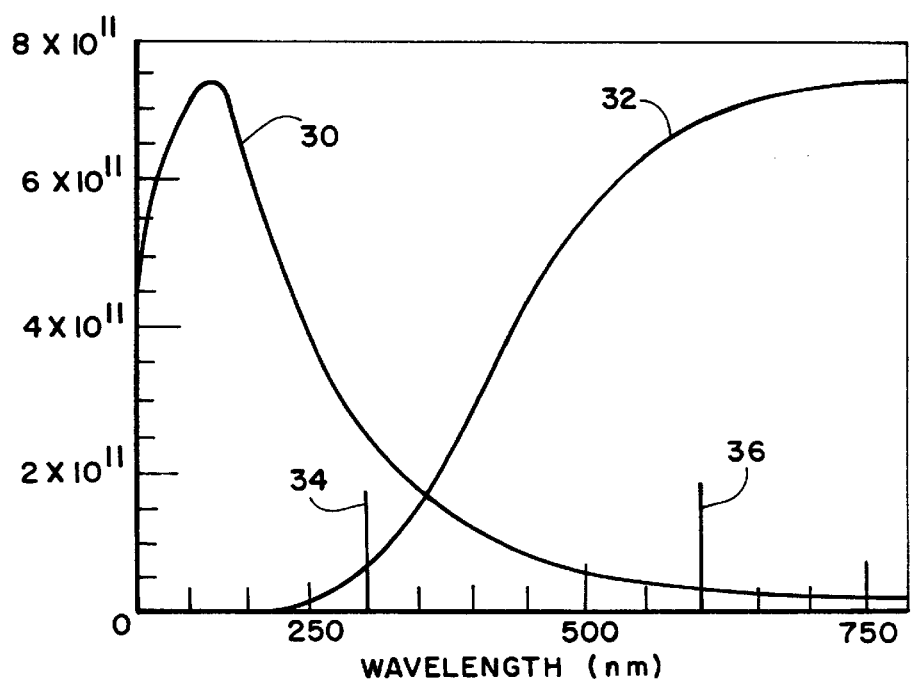
FIG. 4 is a graph illustrating a spectral comparison of the theoretical output of a prior art wall stabilized tube and the expanding plasma energy source of this invention.

FIG. 4 provides a comparison graph between the theoretical output of the expanding plasma emission source system of this invention, curve 30, and the theoretical output of a wall stabilized system, curve 32, exemplified by Hiramoto U.S. Pat. No. 4,464,336. While neither actual spectrum will precisely match the corresponding theoretical spectrum, the comparison of the two curves approximates the actual spectra. The difference is primarily due to the use of a much larger "Q" with the expanding plasma emission source system than with the wall stabilized system. Hiramoto has a Q of about 5.6, using the equation:

$$Q=J/(D \cdot L \cdot t)$$

where:

Q is the energy density,

J is the electric input for a single flash in joules,

D is the bulb (EPES lamp) diameter, cm,

L is the arc length, cm, and t is the pulse width at half the peak height, msec.

Using this same equation, the expanding plasma emission source system of this invention typically has a Q of as high as 800. For best performance, the Q of the system should be at least about 300. As can be seen in FIG. 4, the expanding plasma emission source system spectrum is shifted into the UV range which is critical to organism inactivation. The area to the left of bar 34 delimits the region where the UV operates in the photochemical mode, while the photothermal mode predominates to the right of bar 36. In the photothermal mode region organism kill effectiveness is dominated by the visible and infrared portion of the spectrum, not the UV portion.

Disinfection by UV radiation is accomplished by the photochemical reaction of the cellular nucleic acids. As the UV radiation penetrates the microorganism the energy is absorbed by the organism's deoxyribonucleic acid (DNA), causing structural changes, principally dimerization of thymine. The expanding plasma emission source system of this invention, in microsecond pulses, develops approximately 350 mWs/cm$^2$ at the surface of the quartz cooling tube surrounding the EPES lamp, (mWs=milli-Watt seconds). Intensities decrease in moving away from the tube by a factor of approximately 1/R. A power density of over 10,000,000 mWs/cm$^2$ or an illumination power density well over a million times greater than from typical continuous wave (CW) systems and many times greater than that attainable from a wall stabilized system is achieved with the system of this invention.

When the organisms are hit with such a large number of UV photons in a very short time (approximately 10$^{18}$ photons/cm$^2$ at the closest radius to the EPES lamp) the DNA structure is apparently cross linked and the natural cell damage repair mechanism appears to be disabled. The microorganism is, therefore, rendered unable to reproduce. This inactivation effect is amplified in the expanding plasma emission source system in comparison to CW and wall stabilized pulsed UV systems, due to the high UV power density generated by the elevated operating temperature, high voltage and short pulse duration of the source. This translates into reduced dosage necessary to inactivate various organisms.

Figure 5:
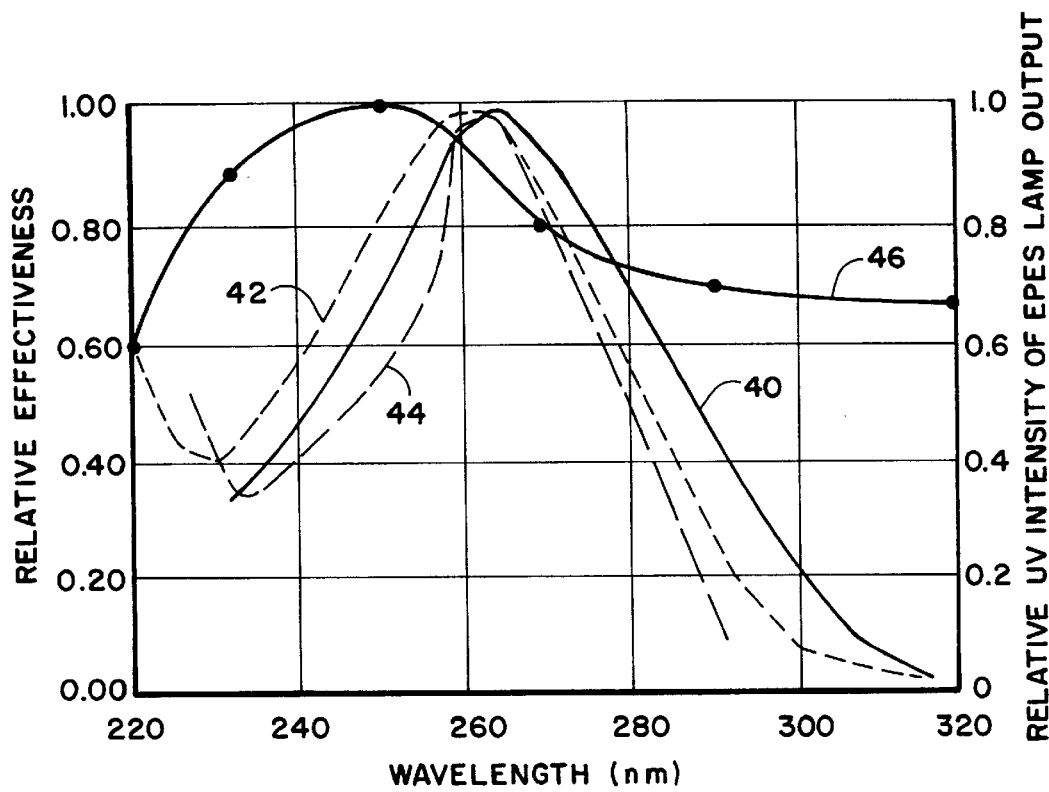
FIG. 5 is a graph comparing the peak UV emission band of the expanding plasma emission source and the maximum absorption bands of significant microorganisms.

FIG. 5 shows curves illustrating the relative effectiveness as a function of the UV light wavelength for germicidal action in general (curve 40), in inactivating E. coli (curve 44) and DNA absorption at different wavelengths (curve 42). Relative effectiveness is indicated along the scale to the left of curves 40, 42 and 44.

Overlaid with these UV inactivation curves is the relative intensity output peak region for the expanding plasma emission source lamp system of this invention (curve 46), with the intensity scale shown along the right edge. This peak is shifted slightly to longer wavelengths than the theoretical peak shown in FIG. 4, since values are averaged measurements over the pulse duration. As can be seen, the peak UV output of the EPES lamp of this invention generally corresponds to the maximum absorption by DNA and the most effective wavelengths for photochemically inactivating E. coli and other microorganisms.

In tests, the pulsed ultraviolet light expanding plasma emission source of this invention, with the very high intensity, short duration pulses has been shown to be effective in inactivating all microorganisms tested, including Cryptosporidium, Giardia, virus and various bacteria including E. coli, Legionella, Pseudomonas, E. aureus and Mycobacteria. The pulsed UV expanding plasma emission source has demonstrated 100% inactivation of Cryptosporidium at levels as low as about 40 mWs/cm$^2$, with even lower energy levels inactivating virus and bacteria.

Figure 6:
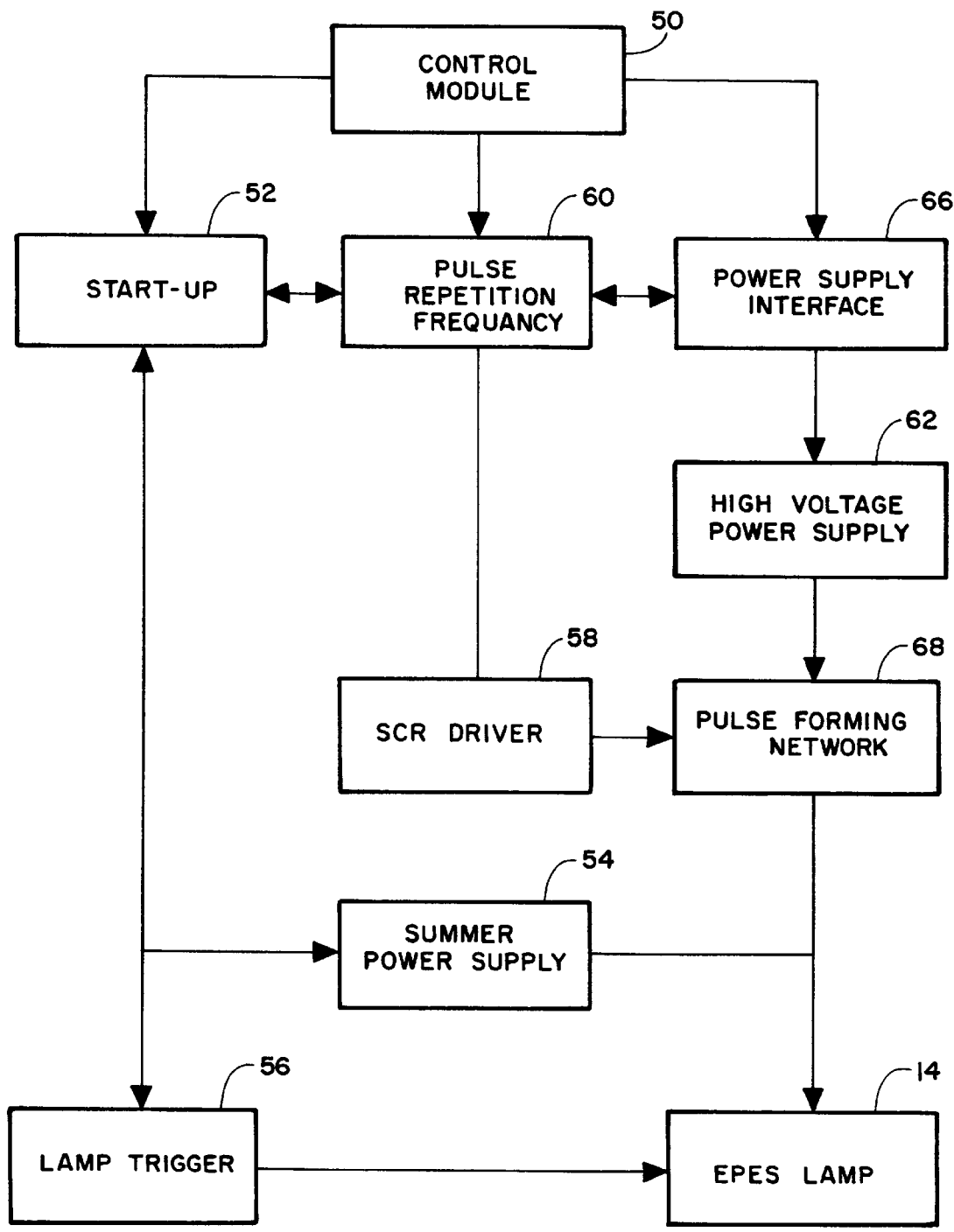
FIG. 6 is a schematic flow diagram of a system for operation of an EPES lamp in accordance with this invention.

FIG. 6 is a schematic block diagram for the electronic control system for the expanding plasma emission source lamp of this invention. The electronic control system 22 as seen in FIG. 1 basically includes nine modules, as shown, each of which is preferably maintained on a separate printed circuit board for ease of replacement and repair, etc.

Power supply module 50 supplies the power to the other modules. Start-up module 52 monitors the condition of the deionized cooling water passing around the expanding plasma emission source of EPES lamp 14 as seen in FIG. 1, and measures the EPES lamp simmer current. The EPES lamp is maintained at a "simmer" level between flashes by a conventional current regulated power supply 54, at a level that maintains a very low temperature plasma within the EPES lamp. When initiation of a flashing cycle is desired, if the EPES lamp temperature and cooling water flow are within predetermined ranges, start-up module 52 allows pulses to be sent to lamp trigger module 56 and silicon controlled rectifier (SCR) module 58 via a pulse repetition frequency module 60 that sets a predetermined pulse frequency rate.

When the lamp starts flashing the start function ceases and cooling water flow and temperature are continuously monitored for equipment safety. Initially, start-up module 52 commands high voltage power supply 62 through power supply interface 66 to a reduced voltage, generally about 70% of the operating voltage. When simmer current is sensed, high voltage power supply 62 is enable to 100% of operating voltage and pulse repetition frequency module 60 is enabled.

Pulse repetition module 60 sends predetermined pulses to the SCR module to flash the EPES lamp 14. During each flash, high voltage power supply 62 is inhibited, with the high voltage power supply enabled after each flash. The frequency of pulsing is determined either from a connection to a flow meter or from a remote control unit which, when connected, disables the flow meter input. Power supply interface module 66 connects to the high voltage power supply 62, sets the operating voltage and enables or inhibits that power supply.

High voltage power supply 62 charges a capacitor located in pulse forming network module 68. Pulse forming network 68 includes two 10 microfarad capacitors. The capacitors are charged to a level up to from about 3000 to 4000 volts (ideally about 3600 volts) and discharge through EPES lamp 14 via a series combination of thyristors or SCRs. The SCRs are mounted on heat sinks and include a conventional arrangement of balancing resistors and snubbers. A reverse biased diode is preferably mounted across the capacitors to prevent current reversal and ringing in the event of a short circuit at EPES lamp 14. Each of the two SCRs receives independent simultaneous gate signals which cause them to conduct and discharge the capacitors. These signals are generated by the SCR driver module on command from pulse repetition module 60. SCR driver 58 typically uses an optical isolator on the input and pulse transformers on the output.

Simmer power supply 54 connects to EPES lamp 14 through the pulse forming network module 68. Diodes are used to protect the relatively low voltage simmer power supply 54 (nominally about 600 volts open circuit and about 140 volts at 3 amps when the lamp is simmering) from the high voltage present on the capacitors. These diodes are mounted on heat sinks with the SCRs. Basically, simmer power supply 54 is an isolation transformer and rectifier with inductive current limiting and a filter capacitor. Preferably, there is a series inductor between the filter bank and the lamp that serves to provide a voltage boost as needed to keep EPES lamp 14 lit following each high current discharge.

Lamp trigger module 56 accepts an optically isolated signal from start-up board 52 and sends a pulse to the primary of a high voltage pulse transformer (such as a Model 132C from EG&G) located close to EPES lamp 14. This transformer in turn generates a pulse of several kilovolts that is applied to a wire (not shown) wrapped around the lamp. That pulse causes the initial ionization of the gas as in other conventional external triggering of flash lamps.

While the overall operating system as shown in FIG. 6 provides excellent performance, any other conventional operating system producing the predetermined flash sequence and the required parameters may be used, if desired.

Figure 7:
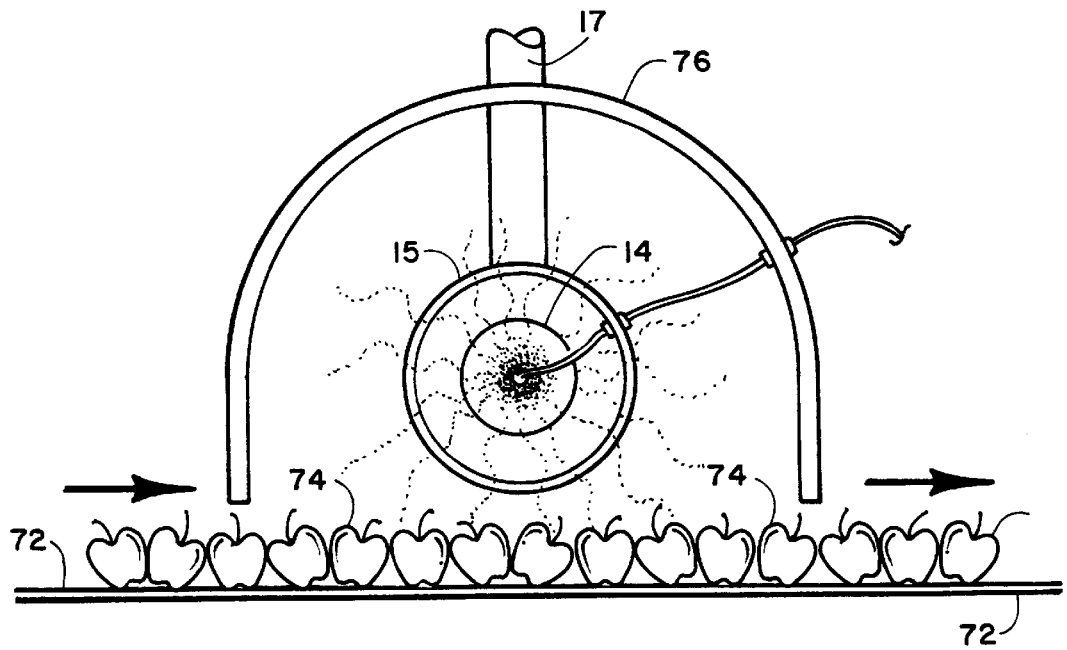
FIG. 7 is a schematic representation of an alternate embodiment of EPES lamp orientation to material being disinfected.

An alternate embodiment for treating material such as solid objects, liquids, flat surfaces, etc. is schematically illustrated in FIG. 7.

An EPES lamp assembly 14 of the sort shown in FIGS. 1 and 2 is positioned in a flow channel or adjacent to a conveyor 72, typically a conventional belt or roller conveyor. Conveyor 72 may include conventional roller means for causing objects 74 to tumble as they are carried along so that all surfaces are exposed to UV radiation from lamp 14.

A cover 76 encloses lamp 14 and an area along conveyor 72, with sufficient space between the cover and conveyor to permit objects 74 to pass unimpeded with the conveyor. Preferably, cover 76 will have a parabolic cross section and a reflective inner surface so as to concentrate UV light on a transverse band across conveyor 72.

Objects 74 may typically be small packages having external surfaces disinfected, fruit or vegetables, such as apples, oranges, carrots and the like, or flat surfaces such as unfolded containers that will have the upper surface disinfected and will be formed into containers later in a sterile atmosphere. Also, conveyor 72 could be a trough for conveying a fluid past lamp 14.

While certain specific relationships, materials and other parameters have been detailed in the above description of preferred embodiments, those can be varied, where suitable, with similar results. Other applications, variation and ramifications of the present invention will occur to those skilled in the art upon reading the present disclosure. Those are intended to be included within the scope of this invention as defined in the appended claims.

I claim:

1. A method of disinfecting a material which consists of the steps of:
   providing an expanding plasma emission source (EPES) lamp having a generally cylindrical inner wall surface and an outer wall surface adjacent to a material to be disinfected;
   pulsing said expanding plasma emission source discharge lamp at from 3000 to 4000 volts for from about 20 to 40 microseconds to generate an expanding plasma having temperatures of from about 15000 to 18000° K. at an energy density Q of at least about 300;
   repeating said pulses at a rate of up to about 30 Hz; and
   terminating each pulse before said plasma equilibrates with said inner wall surface.

2. The method according to claim 1 including mounting said EPES lamp in a pipe and flowing a fluid to be disinfected in a direction past said EPES lamp at a predetermined flow rate.

3. The method according to claim 2 wherein said EPES lamp is mounted axially of said flowing fluid direction.

4. The method according to claim 1 further including conveying objects to be disinfected past EPES lamp in a predetermined direction and mounting said EPES lamp adjacent to said objects being conveyed in.

5. The method according to claim 4 wherein said EPES lamp is mounted transversely to said predetermined direction.

6. The method according to claim 1 wherein said EPES lamp produces ultraviolet light primarily in the 200 to 400 nm range.

7. The method according to claim 1 further including maintaining a plasma in said EPES lamp between said flashes at a simmer, power level.

8. An apparatus for disinfecting a material which comprises:
   means for carrying material to be treated in a predetermined direction;
   an expanding plasma emission source lamp positioned adjacent to said moving means;
   said expanding plasma emission source lamp having inner and outer wall surfaces;
   means for imposing a voltage pulse of from about 3000 to 4000 volts on said expanding plasma emission source lamp to generate an expanding plasma pulse having a duration of about 20 to 40 microseconds at temperatures of from about 15000 to 18000° K. at an energy density Q, of at least about 300;
   means for repeating said pulse at intervals up to about 30 Hz; and
   means for terminating said pulse after said expanding plasma emission source lamp is substantially filled with said plasma but before said plasma stabilizes with said inner expanding plasma emission source lamp wall surface.

9. The apparatus according to claim 8 wherein said means for imposing a high voltage pulse generates ultraviolet light primarily in the 200 to 400 nm range.

10. The apparatus according to claim 8 further including means for maintaining a plasma at a simmer, power level between said high voltage pulses.

11. The apparatus according to claim 8 including means for mounting said EPES lamp in a pipe and means for flowing a fluid to be disinfected past said EPES lamp at a predetermined flow rate.

12. The apparatus according to claim 11 wherein said mounting means mounts EPES lamp axially of said fluid flowing direction.

13. The apparatus according to claim 8 further including a conveyor means for conveying objects to be disinfected past said EPES lamp in a predetermined direction.

14. The method according to claim 8 wherein said EPES lamp is mounted transversely to said predetermined direction.

* * * * *